(12) United States Patent
White et al.

(10) Patent No.: US 10,978,189 B2
(45) Date of Patent: Apr. 13, 2021

(54) DIGITAL REPRESENTATIONS OF PAST, CURRENT, AND FUTURE HEALTH USING VECTORS

(71) Applicant: Optum, Inc., Minnetonka, MN (US)

(72) Inventors: Patrick White, Gladstone, NJ (US); Somadev Pasala, Montclair, NJ (US); Donald Johnson, Newton, NJ (US); Sreedhar Potturi, Bridgewater, NJ (US); Dhaval Shah, North Brunswick, NJ (US); Anthony Degliomini, Livingston, NJ (US); Michael Brennan, Morris Plains, NJ (US)

(73) Assignee: Optum, Inc., Minnetonka, MN (US)

( * ) Notice: Subject to any disclaimer, the term of this patent is extended or adjusted under 35 U.S.C. 154(b) by 364 days.

(21) Appl. No.: 16/205,891

(22) Filed: Nov. 30, 2018

(65) Prior Publication Data
US 2020/0027531 A1    Jan. 23, 2020

Related U.S. Application Data

(60) Provisional application No. 62/700,602, filed on Jul. 19, 2018.

(51) Int. Cl.
*G16H 10/60*    (2018.01)
*G06F 40/295*   (2020.01)
(Continued)

(52) U.S. Cl.
CPC .......... *G16H 10/60* (2018.01); *G06F 40/295* (2020.01); *G06N 20/10* (2019.01); *G06T 19/00* (2013.01);
(Continued)

(58) Field of Classification Search
CPC ........ G16H 10/60; G16H 50/20; G16H 50/30; G06F 40/295; G06F 40/20; G06F 40/30;
(Continued)

(56) References Cited

U.S. PATENT DOCUMENTS

| 6,266,645 B1 | 7/2001 | Simpson |
| 6,556,977 B1 | 4/2003 | Lapointe et al. |

(Continued)

FOREIGN PATENT DOCUMENTS

WO    2014/201515 A1    12/2014

OTHER PUBLICATIONS

U.S. Patent and Trademark Office, NonFinal Office Action for U.S. Appl. No. 15/927,188, dated May 26, 2020, (35 pages), USA.

(Continued)

*Primary Examiner* — Eliza A Lam
(74) *Attorney, Agent, or Firm* — Alston & Bird LLP

(57) ABSTRACT

A computing entity accesses instances of medical information corresponding to a population of patients and generates a plurality of medical sentences corresponding to the population by, for each patient of the population, generating one medical sentence corresponding to the patient and a timestamp associated with each instance such that the one medical sentence comprises one or more medical codes in a chronological order. The computing entity generates a vector dictionary comprising a plurality of multi-dimensional vectors based on a vector generation model trained using machine learning and the plurality of medical sentences with each multi-dimensional vector corresponding to a medical code. The computing entity generates a digital representation of a first patient of the population using an anagram model and the vector dictionary, determines a health state of (Continued)

the first patient based on the digital representation, and provides an output indicating the health state of the first patient.

20 Claims, 7 Drawing Sheets

(51) Int. Cl.
*G06T 19/00* (2011.01)
*G16H 50/20* (2018.01)
*G06N 20/10* (2019.01)
*G06N 3/08* (2006.01)
*G06F 40/20* (2020.01)
*G16H 50/30* (2018.01)

(52) U.S. Cl.
CPC ......... *G16H 50/20* (2018.01); *G06T 2200/24* (2013.01); *G06T 2219/004* (2013.01)

(58) Field of Classification Search
CPC ................ G06T 19/00; G06T 2200/24; G06T 2219/004; G06N 20/10; G06N 3/088
See application file for complete search history.

(56) References Cited

U.S. PATENT DOCUMENTS

| | | | |
|---|---|---|---|
| 6,915,254 B1 | 7/2005 | Heinze et al. | |
| 7,351,203 B2* | 4/2008 | Jelliffe | A61B 5/7275 600/301 |
| 7,499,048 B2 | 3/2009 | Sieracki et al. | |
| 7,801,839 B2 | 9/2010 | Kates et al. | |
| 8,255,412 B2 | 8/2012 | Gao et al. | |
| 8,296,247 B2 | 10/2012 | Zhang et al. | |
| 8,320,651 B2 | 11/2012 | Vining et al. | |
| 8,504,392 B2 | 8/2013 | Saria et al. | |
| 8,856,156 B1 | 10/2014 | McNair et al. | |
| 8,963,914 B2 | 2/2015 | Rawat et al. | |
| 9,805,160 B2 | 10/2017 | Morris et al. | |
| 9,828,671 B2 | 11/2017 | Shibusawa et al. | |
| 10,176,645 B2 | 1/2019 | Canfield et al. | |
| 2005/0240439 A1 | 10/2005 | Covit et al. | |
| 2008/0288292 A1 | 11/2008 | Bi et al. | |
| 2012/0033871 A1 | 2/2012 | Vining et al. | |
| 2012/0166212 A1 | 6/2012 | Campbell | |
| 2012/0185275 A1 | 7/2012 | Loghmani | |
| 2013/0080187 A1 | 3/2013 | Bacon et al. | |
| 2014/0249849 A1 | 9/2014 | Khare et al. | |
| 2014/0278490 A1 | 9/2014 | Namazifar et al. | |
| 2015/0088870 A1* | 3/2015 | Jayasundera | G16H 50/20 707/723 |
| 2015/0095016 A1 | 4/2015 | Karres et al. | |
| 2015/0356198 A1 | 12/2015 | D'Souza et al. | |
| 2016/0012202 A1 | 1/2016 | Hu et al. | |
| 2016/0063214 A1 | 3/2016 | Blue | |
| 2016/0092641 A1 | 3/2016 | Delaney et al. | |
| 2017/0132288 A1 | 5/2017 | Ho et al. | |
| 2017/0161619 A1 | 6/2017 | Franceschini et al. | |
| 2017/0308981 A1 | 10/2017 | Razavian et al. | |
| 2018/0025121 A1 | 1/2018 | Fei et al. | |
| 2018/0089382 A1 | 3/2018 | Allen et al. | |
| 2018/0089383 A1 | 3/2018 | Allen et al. | |
| 2018/0165418 A1 | 6/2018 | Swartz et al. | |
| 2018/0233233 A1* | 8/2018 | Sharma | G16H 50/30 |
| 2018/0260381 A1 | 9/2018 | Carreras et al. | |
| 2018/0293499 A1 | 10/2018 | He et al. | |
| 2018/0315440 A1 | 11/2018 | Inaba et al. | |
| 2019/0005019 A1 | 1/2019 | Burke et al. | |
| 2019/0096140 A1 | 3/2019 | Canfield et al. | |
| 2019/0114318 A1 | 4/2019 | Zhou et al. | |
| 2019/0171792 A1 | 6/2019 | Manica et al. | |
| 2019/0188271 A1 | 6/2019 | Murdock et al. | |
| 2019/0188848 A1 | 6/2019 | Madani et al. | |
| 2019/0220694 A1 | 7/2019 | Biswas et al. | |
| 2019/0236206 A1 | 8/2019 | Chowdhury et al. | |
| 2019/0251084 A1 | 8/2019 | Wang et al. | |
| 2019/0286759 A1 | 9/2019 | Wilkins et al. | |
| 2020/0034366 A1 | 1/2020 | Kivatinos et al. | |
| 2020/0251219 A1 | 8/2020 | Fukunishi | |

OTHER PUBLICATIONS

Wang et al., "Diagnosis Code Assignment Using Sparsity-Based Disease Correlation Embedding," Journal of Latex Class Files, vol. 13, No. 9, Sep. 2014, pp. 1-13.

Shubham Agarwal, Word to Vectors—Natural Language Processing, May 18, 2017, https://towardsdatascience.com/word-to-vectors-natural-language-processing-b253dd0b0817, Apr. 17, 2019.

Pakhomov, S., et al., Automating the Assignment of Diagnosis Codes to Patient Encounters Using Example-based and Machine Learning Techniques, Sep. 1, 2006, Journal of the American Medical Informatics Association, 516-525, 13/5, https://watermark.silverchair.com/13-5-516.pdf?token=AQECAHi208BE49oan9kkhW_Ercy7Dm3ZL_9Cf3qfKAc485ys . . . .

Okamoto, K., et al., Automatic DPC code selection from discharge summaries using several machine learning methods, Dec. 1, 2011, Transactions of Japanese Society for Medical and Biological Engineering, 40-47, 49/1, https://www.jstage.jst.go.jp/article/jsmbe/49/1/49_1_40/_pdf/-char/ja, Aug. 14, 2018 (Japanese Article—English Abstract Only).

Lingren, T., et al., Electronic Health Record Based Algorithm to Identify Patients with Autism Spectrum Disorder, Jul. 29, 2016, PLOS ONE, 1-16, http://nrs.harvard.edu/um-3:HUL.InstRepos:29002605, Aug. 14, 2018.

Jara, J. L., et al., Empirical evaluation of three machine learning method for automatic classification of neoplastic diagnoses/ Evaluación empírica de tres métodos de aprendizaje automático para clasificar automáticamente diagnósticos de neoplasias, Dec. 1, 2011, Ingeniare. Revista chilena de ingenieria, 359-368, 19/3, https://scielo.conicyt.cl/pdf/ingeniare/v19n3/art06.pdf, Aug. 14, 2018.

Gonzenbach, "Sentiment Classification and Medical Health Record Analysis Using Convolutional Neural Networks," Swiss Federal Institute of Technology Zurich, May 24, 2016, pp. 1-56.

United States Patent and Trademark Office, Notice of Allowance for U.S. Appl. No. 15/927,188, dated Sep. 22, 2020, (10 pages), U.S.

Bui Alex A.T. et al. "Medical Data Visualization: Toward Integrated Clinical Workstations," InMedical Imaging Informatics, (2010), pp. 139-193. Springer, Boston, MA. DOI: 10.1007/978-1-4419-0385-3_4.

Diseases of the Respiratory System: (ICD-10-CM Chapter 10, Codes J00-J99), General Surgery, Basicmedical Key, Jun. 3, 2017. [Retrieved from the Internet Feb. 23, 2020] <URL: https://basicmedicalkey.com/diseases-of-the-respiratory-system-icd-10-cm-chapter-10-codes-j00-j99/>.

Shi, Liehang et al. "Three-Dimensional Visual Patient Based on Electronic Medical Diagnostic Records," IEEE Journal of Biomedical and Health Informatics, vol. 22, No. 1, Jan. 2018, pp. 161-172.

Feng, Yujuan et al. "Patient Outcome Prediction Via Convolutional Neural Networks Based on Multi-Granularity Medical Concept Embedding," 2017 IEEE International Converence on Bioinformatics and Biomedicine (BIBM), Nov. 13, 2017, pp. 770-777.

International Searching Authority, International Search Report and Written Opinion for International Application No. PCT/US2019/041784, dated Nov. 27, 2019, (18 pages), European Patent Office, Rijswijk, The Netherlands.

* cited by examiner

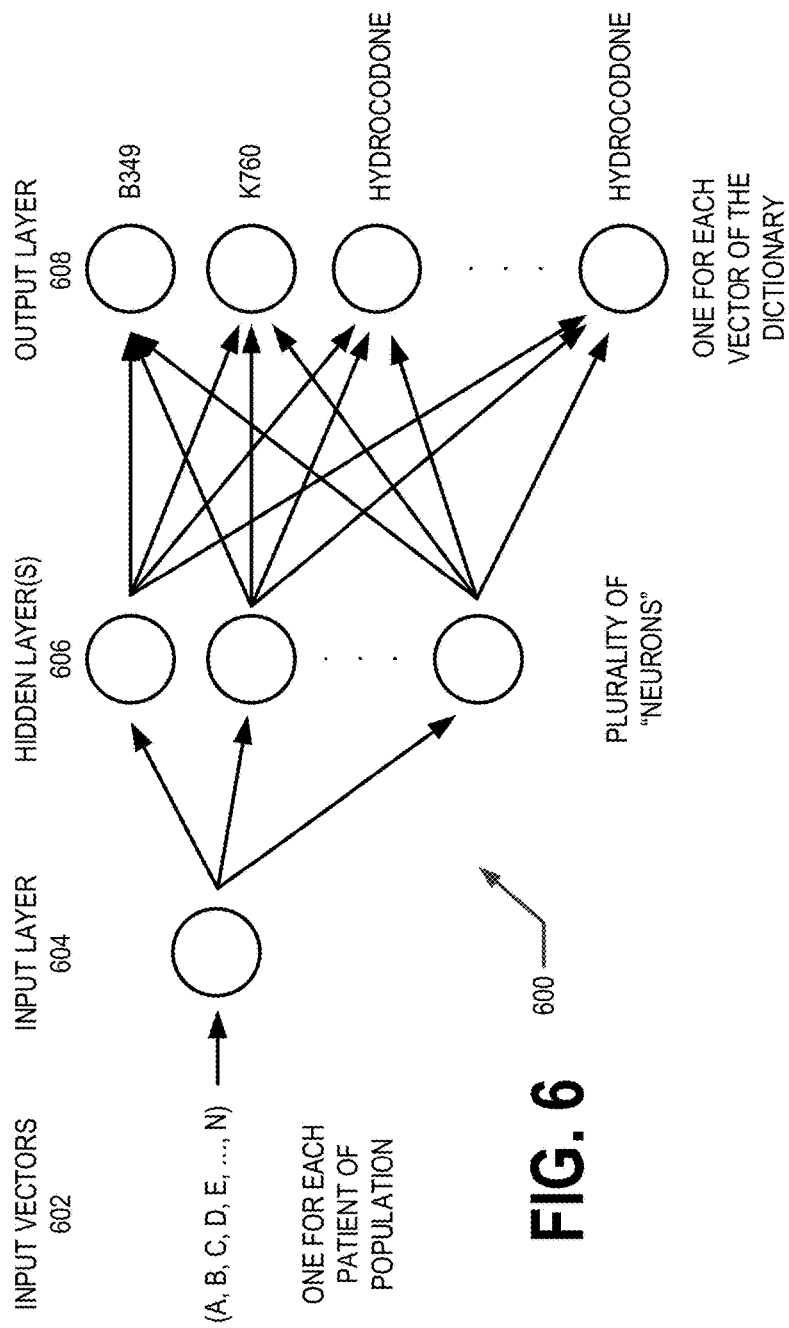

DIGITAL REPRESENTATIONS OF PAST, CURRENT, AND FUTURE HEALTH USING VECTORS

CROSS-REFERENCE TO RELATED APPLICATIONS

This application claims priority to U.S. Application No. 62/700,602, filed Jul. 19, 2018, the content of which is incorporated herein by reference in its entirety.

FIELD

Various embodiments relate generally to generating and/or using a digital representation of a patient. An example embodiment provides and/or generates a multi-dimensional vector representing a patient's medical history for use in, for example, medical prediction modeling.

BACKGROUND

Medical information is often encoded using medical codes, such as diagnoses codes, procedure codes, prescription or drug codes, equipment codes, revenue codes, place of service codes, and/or the like. These medical codes are non-interpretable, alpha-numeric strings that can be quite specific. For example, a fracture of the left forearm may have a specific code that is different from the code for a fracture of the right forearm. Thus, trying to identify cohorts of similar patients or patients having similar health histories may be quite difficult. For example, a key word search may identify groups of patients that have one element of their medical histories in common, but that have generally different health histories and/or conditions. For example, two patients may both have type 2 diabetes, but are vastly different in their underlying health conditions. Additionally, type 2 diabetes is highly correlated to hypertension, but people with hypertension would be considered as an unrelated population according to the key word search strategy.

BRIEF SUMMARY

Various embodiments provide methods, apparatuses, computer program products, systems, and/or the like that provide a digital healthcare twin which is a digital representation of a patient's medical history. In an example embodiment, the digital representation of the patient's medical history is a vector within a multi-dimensional space. In various embodiments, medical information/data corresponding to a population of patients (e.g., a plurality of patients) is accessed and a medical sentence for each patient of the population of patients are formed therefrom. In various embodiments, the medical sentences consist of plurality of medical codes (e.g., diagnosis codes, procedure codes, prescription or drug codes, equipment codes, revenue codes, place of service codes, and/or the like). Each patient of the population of patients is represented by one medical sentence and each medical sentence has a preset length (e.g., a particular number of medical codes). In an example embodiment, when a first medical sentence corresponding to a first patient has fewer than the particular number of medical codes, dummy medical codes may be added to the first medical sentence so that the first medical sentence will comprise the particular number of medical codes. In an example embodiment, the medical codes of the medical sentence are in chronological order based on when the corresponding medical events occurred. The medical sentences are then used to train a vector generation model. For example, the vector generation model may be trained using machine learning and a training data set comprising at least some of the medical sentences. The vector generation model may provide a digital representation of one or more patients of the population of patients and/or a vector dictionary corresponding to the vocabulary items (e.g., unique medical codes) of the medical sentences used to train the vector generation model.

In various embodiments, the vector generation model and/or another module (e.g., using a vector dictionary generated by the vector generation model) generates a digital representation for the patients of the population of patients. In various embodiments, the digital representation of the patient is used to determine a current health state of the patient. In various embodiments, the digital representation of the patient, an anagram model, the multi-dimensional vectors of the vector dictionary, a digital representation of a cohort of patients having similar medical histories to the patient, and/or the like, are used to determine a possible future health state for the patient. The possible future health state may be an optimal health state of the patient given the first patient's medical history, an expected future health state of the patient (e.g., determined based on digital representations of a cohort of patients having similar medical histories as the patient), a predicted result of a medical decision for the patient, and/or the like. In various embodiments, the current health state and/or the possible future health state for the patient are provided via an interactive user interface of a user computing entity and may influence one or more decisions regarding medical treatment of the patient.

According to one aspect of the present invention, a method for providing a health state of a first patient is provided. In an example embodiment, the method comprises accessing, by a computing entity comprising a processor and a memory storing computer program code, a plurality of instances of medical information encoded using medical codes and corresponding to a population of patients comprising a plurality of patients. The method further comprises generating, by the computing entity, a plurality of medical sentences corresponding to the population of patients by, for each patient of the population of patients, generating one medical sentence based on one or more instances of the plurality of instances of medical information corresponding to the patient and a timestamp associated with each instance of the one or more instances such that the one medical sentence corresponding to the patient comprises one or more medical codes in a chronological order. The method further comprises generating, by the computing entity, a vector dictionary comprising a plurality of multi-dimensional vectors (a) based on a vector generation model trained using machine learning and the plurality of medical sentences, and (b) in a multi-dimensional space having a configurable dimensionality. Each multi-dimensional vector corresponds to a medical code. The method further comprises generating, by the computing entity, a digital representation of a first patient of the population of patients using an anagram model and the multi-dimensional vectors of the vector dictionary; determining, by the computing entity, a health state of the first patient based on the digital representation of the first patient; and providing, by the computing entity, an output indicating the health state of the first patient.

According to another aspect of the present invention, an apparatus is provided. In an example embodiment, the apparatus comprises at least one processor and at least one memory including computer program code for one or more programs. The at least one memory and the computer program code are configured to, with the at least one processor, cause the apparatus to at least access a plurality of instances of medical information encoded using medical codes and corresponding to a population of patients comprising a plurality of patients; generate a plurality of medical sentences corresponding to the population of patients by, for each patient of the population of patients, generating one medical sentence based on one or more instances of the plurality of instances of medical information corresponding to the patient and a timestamp associated with each instance of the one or more instances such that the one medical sentence corresponding to the patient comprises one or more medical codes in a chronological order; generate a vector dictionary comprising a plurality of multi-dimensional vectors (a) based on a vector generation model trained using machine learning and the plurality of medical sentences, and (b) in a multi-dimensional space having a configurable dimensionality, each multi-dimensional vector corresponding to a medical code; generate a digital representation of a first patient of the population of patients using an anagram model and the multi-dimensional vectors of the vector dictionary; determine a health state of the first patient based on the digital representation of the first patient; and provide an output indicating the health state of the first patient.

According to yet another aspect of the present invention, a computer program product is provided. In an example embodiment, the computer program product comprises at least one non-transitory computer-readable storage medium having computer-executable program code portions stored therein. The computer-executable program code portions comprise program code instructions. The computer program code instructions, when executed by a processor of a computing entity, are configured to cause the computing entity to at least access a plurality of instances of medical information encoded using medical codes and corresponding to a population of patients comprising a plurality of patients; generate a plurality of medical sentences corresponding to the population of patients by, for each patient of the population of patients, generating one medical sentence based on one or more instances of the plurality of instances of medical information corresponding to the patient and a timestamp associated with each instance of the one or more instances such that the one medical sentence corresponding to the patient comprises one or more medical codes in a chronological order; generate a vector dictionary comprising a plurality of multi-dimensional vectors (a) based on a vector generation model trained using machine learning and the plurality of medical sentences, and (b) in a multi-dimensional space having a configurable dimensionality, each multi-dimensional vector corresponding to a medical code; generate a digital representation of a first patient of the population of patients using an anagram model and the multi-dimensional vectors of the vector dictionary; determine a health state of the first patient based on the digital representation of the first patient; and provide an output indicating the health state of the first patient.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

Figure 4:
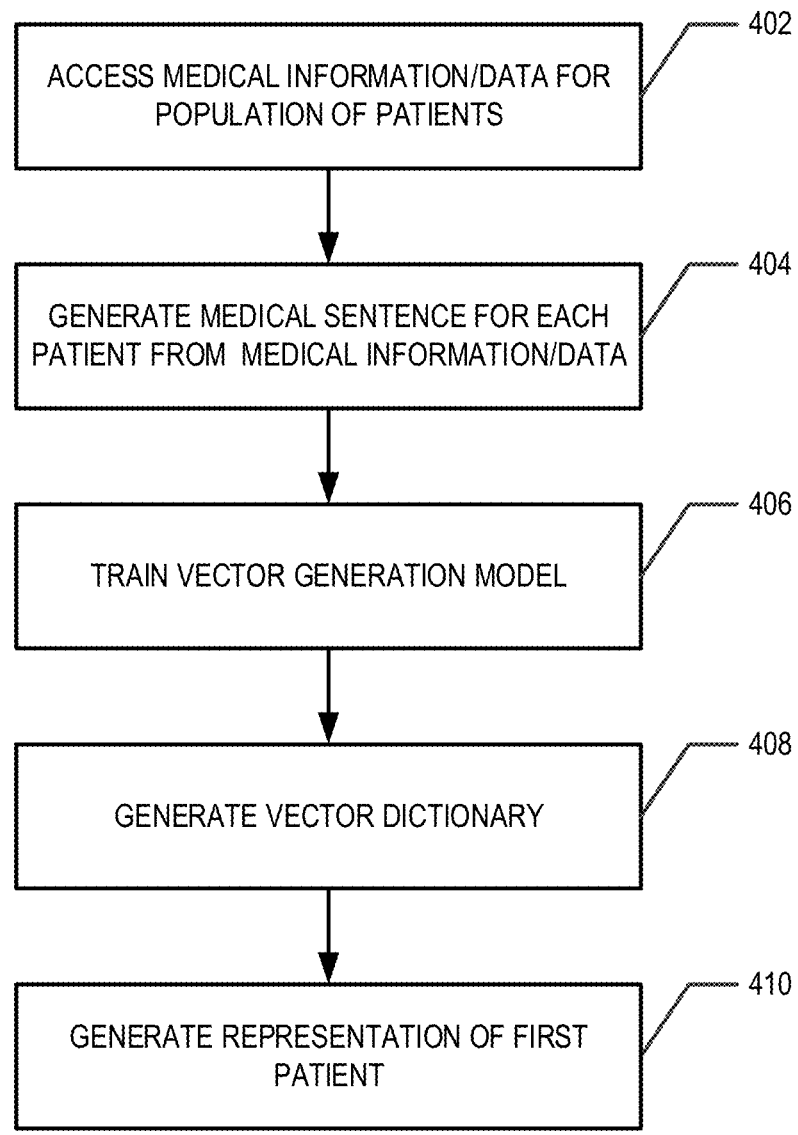
Figure 7A:
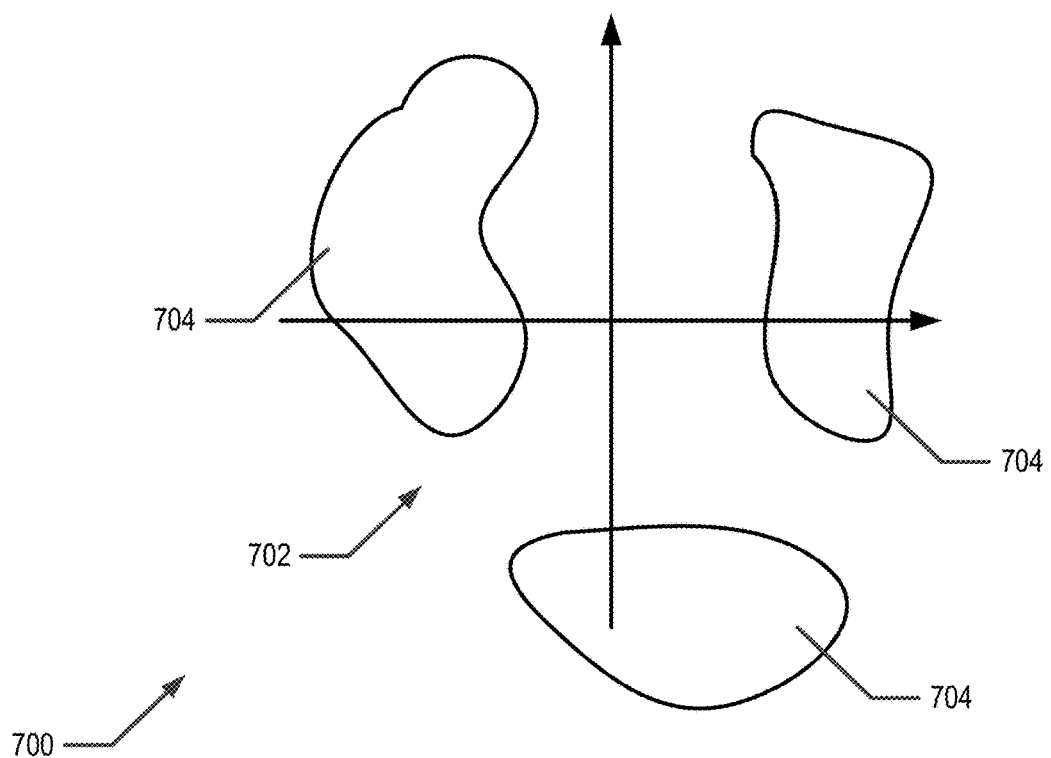
Figure 7B:
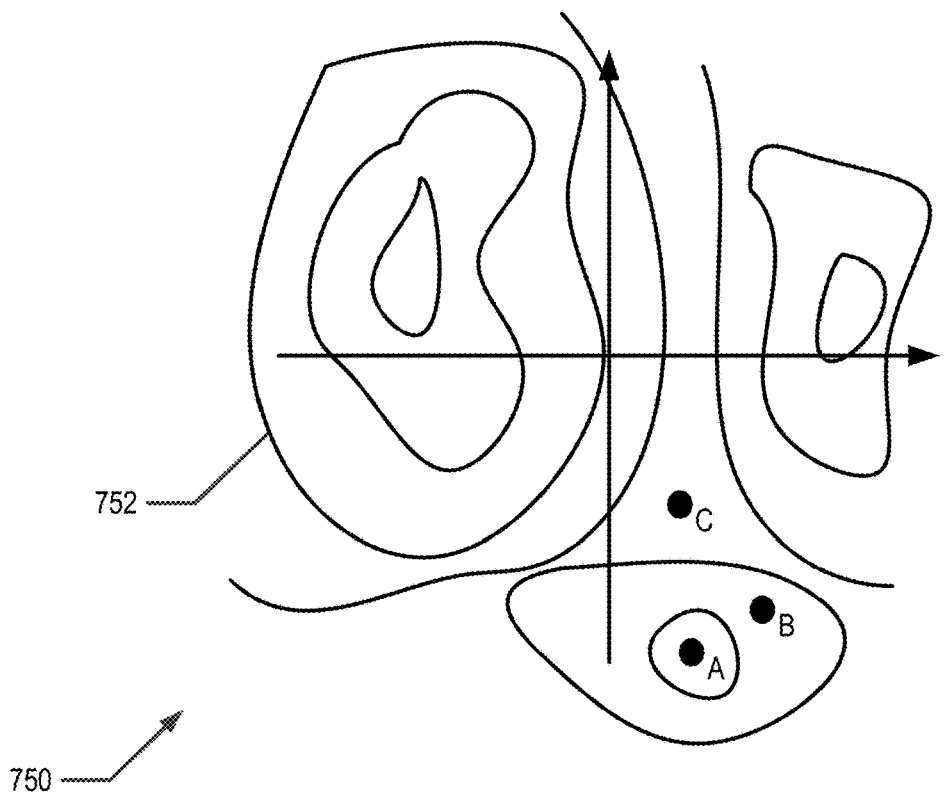
Figure 8:
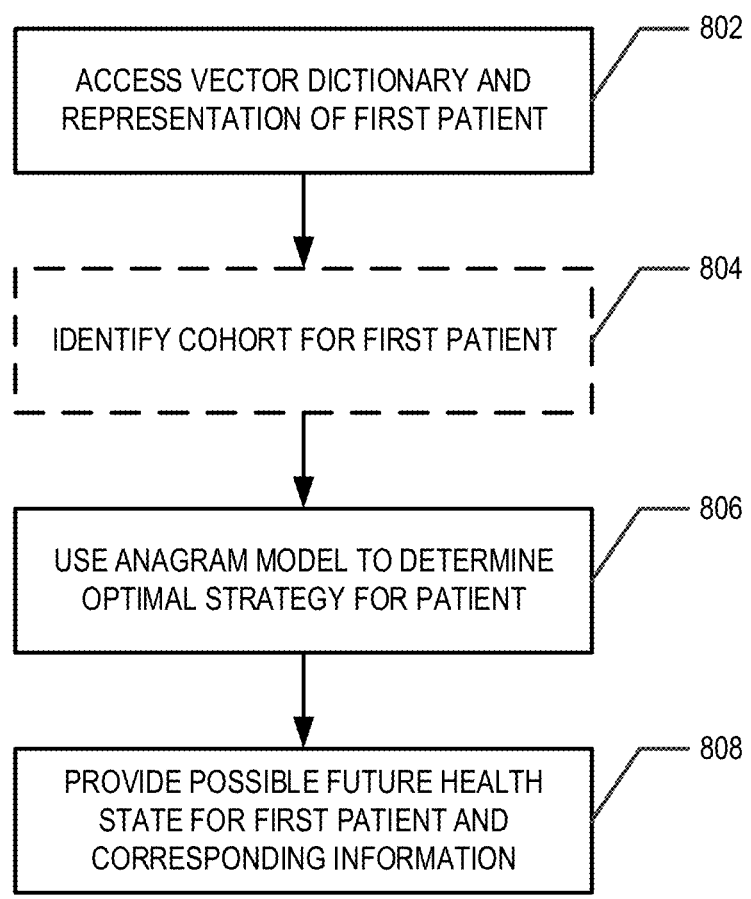

FIG. 4 provides a flowchart illustrating example procedures, processes, and/or operations performed by a computing entity to provide a digital representation of a first patient and a corresponding health state for the first patient, in accordance with an example embodiment of the present invention;

FIG. 5 illustrates an example medical sentence and training window used to train a vector generation model, in accordance with an example embodiment of the present invention;

FIG. 6 is a schematic of a vector generation model, in accordance with an example embodiment of the present invention;

FIGS. 7A and 7B illustrate healthful and unhealthful regions of a multi-dimensional space and a health topology of a multi-dimensional space, respectively, according to example embodiments of the present invention; and FIG. 8 provides a flowchart illustrating example procedures, processes, and/or operations performed by a computing entity to determine a possible future health state for a first patient, in accordance with an example embodiment of the present invention.

DETAILED DESCRIPTION OF SOME EXAMPLE EMBODIMENTS

Various embodiments of the present invention now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" (also designated as "/") is used herein in both the alternative and conjunctive sense, unless otherwise indicated. The terms "illustrative" and "exemplary" are used to be examples with no indication of quality level. Like numbers refer to like elements throughout.

I. General Overview

In various embodiments, methods, systems, apparatuses, computer program products, and/or the like are provided for providing digital representations for one or more patients. In an example embodiment, a digital representation of a patient is a vector defined in a multi-dimensional space. For example, the digital representation of the patient may be an ordered list of numbers that encodes the patient's current health state. In various embodiments, the digital representation of the patient is generated using a vector generation model. In an example embodiment, the vector generation model is configured to receive a plurality of input medical sentences and provide output comprising a multi-dimensional vector corresponding to each vocabulary item (e.g., each unique medical code) of the plurality of input medical sentences. In an example embodiment, each patient is represented by one medical sentence. The medical sentence comprises a particular number of medical codes that are in chronological order based on the order of the occurrence of events corresponding to the medical codes. Medical sentences having fewer than the particular number of medical codes are expanded to include the particular number of medical codes by adding dummy codes to the medical sentence until the medical sentence comprises the particular number of medical codes. The vector generation model may then be trained, using the medical sentences. The digital representation of the patient is the ordered combination of vectors corresponding to the patient's medical sentence.

Various embodiments further comprise use of an anagram model to determine and/or simulate a possible future health state of a patient. In an example embodiment, using an anagram model comprises combining the digital representation of the patient with one or more multi-dimensional vectors from the vector dictionary to simulate the possible future health state of the patient and/or applying one or more anagram relationships identified within the vector dictionary to the digital representation of the patient. In an example embodiment, the possible future health state of the patient may be determined based on the digital representations of a cohort of patients having medical histories similar to the medical history of the patient, the vectors of the vector dictionary, one or more anagram relationships identified within the vector dictionary, and/or the like. In various embodiments, the possible future health state of the patient is an optimal health state of the patient given the patient's medical history, an expected future health state determined based on digital representations of a cohort of patients having similar medical histories as the patient, a predicted result of a medical decision for the patient, and/or the like. The patient's current health state and/or possible future health state may be provided (e.g., via an interactive user interface of a user computing entity). In an example embodiment, one or more decisions regarding current and/or future treatment of the patient may be determined based on patient's current or possible future health state.

II. Computer Program Products, Methods, and Computing Entities

Embodiments of the present invention may be implemented in various ways, including as computer program products that comprise articles of manufacture. Such computer program products may include one or more software components including, for example, software objects, methods, data structures, and/or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of a data structure, apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

III. Exemplary System Architecture

Figure 1:
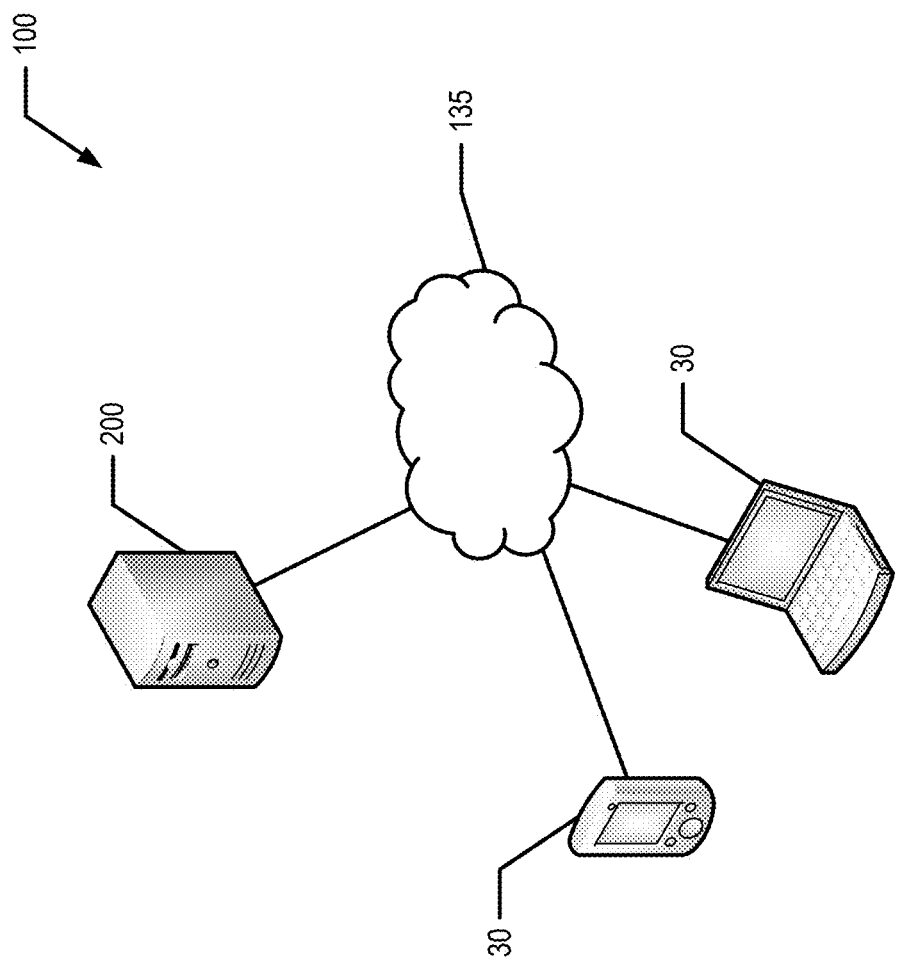
FIG. 1 is a diagram of a system that can be used to practice various embodiments of the present invention.

FIG. 1 provides an illustration of a system 100 that can be used in conjunction with various embodiments of the present invention. As shown in FIG. 1, the system 100 may comprise one or more computing entities 200, one or more user computing entities 30, one or more networks 135, and/or the like. Each of the components of the system may be in electronic communication with, for example, one another over the same or different wireless or wired networks 135 including, for example, a wired or wireless Personal Area Network (PAN), Local Area Network (LAN), Metropolitan Area Network (MAN), Wide Area Network (WAN), and/or the like. Additionally, while FIG. 1 illustrate certain system entities as separate, standalone entities, the various embodiments are not limited to this particular architecture.

a. Exemplary Computing Entity

Figure 2:
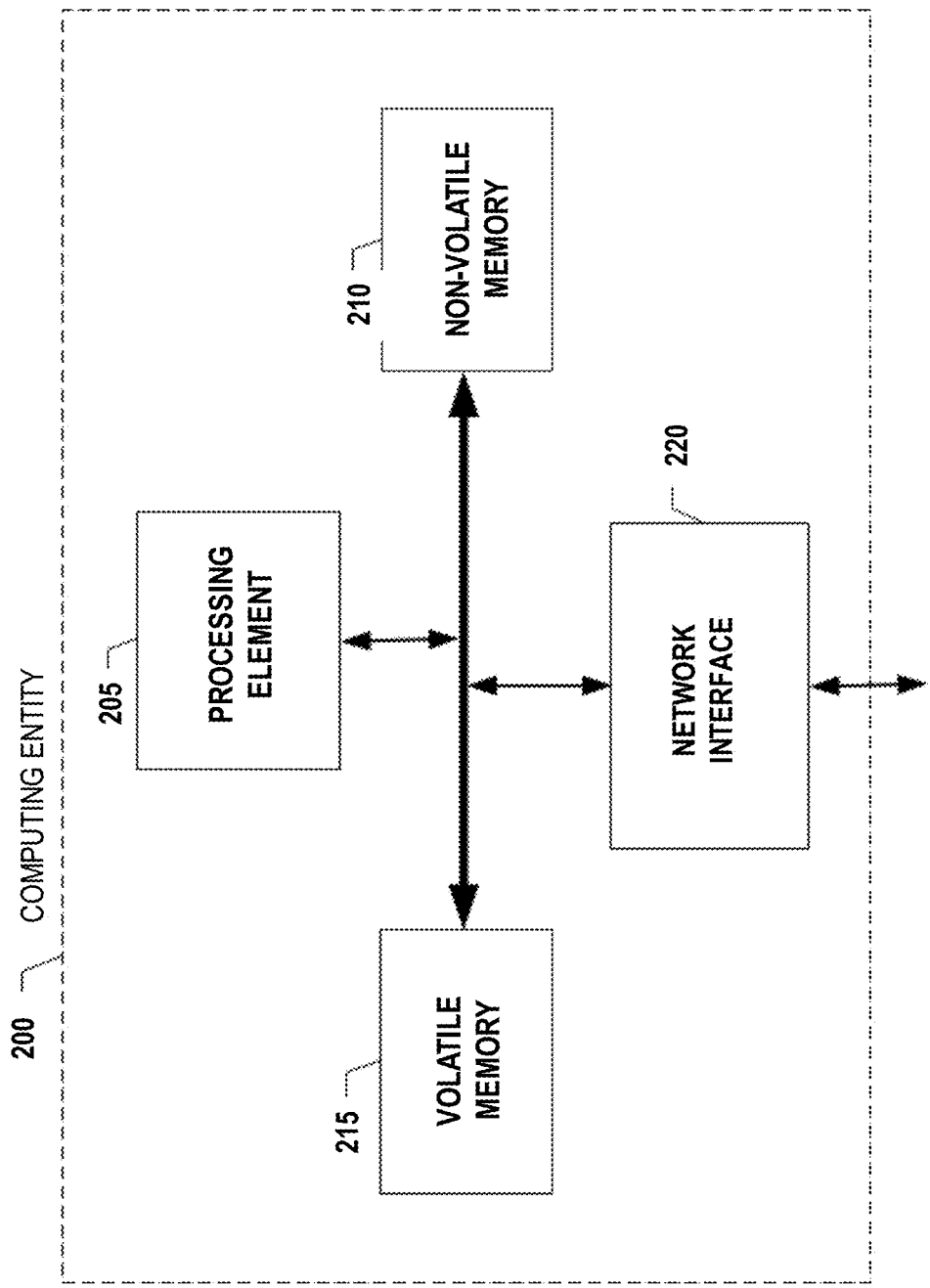
FIG. 2 is a schematic of a computing entity in accordance with certain embodiments of the present invention.

FIG. 2 provides a schematic of a computing entity 200 according to one embodiment of the present invention. In general, the terms computing entity, entity, device, system, and/or similar words used herein interchangeably may refer to, for example, one or more computers, computing entities, desktop computers, mobile phones, tablets, phablets, notebooks, laptops, distributed systems, items/devices, terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the computing entity 200 may also include one or more network and/or communications interfaces 220 for communicating with various computing entities, such as by communicating data, content, information, and/or similar terms used herein interchangeably that can be transmitted, received, operated on, processed, displayed, stored, and/or the like. For instance, the computing entity 200 may communicate with other computing entities 200, one or more user computing entities 30, and/or the like.

As shown in FIG. 2, in one embodiment, the computing entity 200 may include or be in communication with one or more processing elements 205 (also referred to as processors, processing circuitry, and/or similar terms used herein interchangeably) that communicate with other elements within the computing entity 200 via a bus, for example. As will be understood, the processing element 205 may be embodied in a number of different ways. For example, the processing element 205 may be embodied as one or more complex programmable logic devices (CPLDs), microprocessors, multi-core processors, coprocessing entities, application-specific instruction-set processors (ASIPs), and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like. As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the computing entity 200 may further include or be in communication with non-volatile media (also referred to as non-volatile storage, memory, memory storage, memory circuitry and/or similar terms used herein interchangeably). In one embodiment, the non-volatile storage or memory may include one or more non-volatile storage or memory media 210 as described above, such as hard disks, ROM, PROM, EPROM, EEPROM, flash memory, MMCs, SD memory cards, Memory Sticks, CBRAM, PRAM, FeRAM, RRAM, SONOS, racetrack memory, and/or the like. As will be recognized, the non-volatile storage or memory media may store databases, database instances, database management system entities, data, applications, programs, program modules, scripts, source code, object code, byte code, compiled code, interpreted code, machine code, executable instructions, and/or the like. The term database, database instance, database management system entity, and/or similar terms used herein interchangeably may refer to a structured collection of records or information/data that is stored in a computer-readable storage medium, such as via a relational database, hierarchical database, and/or network database.

In one embodiment, the computing entity 200 may further include or be in communication with volatile media (also referred to as volatile storage, memory, memory storage, memory circuitry and/or similar terms used herein interchangeably). In one embodiment, the volatile storage or memory may also include one or more volatile storage or memory media 315 as described above, such as RAM, DRAM, SRAM, FPM DRAM, EDO DRAM, SDRAM, DDR SDRAM, DDR2 SDRAM, DDR3 SDRAM, RDRAM, VRAM, cache memory, register memory, and/or the like. As will be recognized, the volatile storage or memory media may be used to store at least portions of the databases, database instances, database management system entities, data, applications, programs, program modules, scripts, source code, object code, byte code, compiled code, interpreted code, machine code, executable instructions, and/or the like being executed by, for example, the processing element 305. Thus, the databases, database instances, database management system entities, data, applications, programs, program modules, scripts, source code, object code, byte code, compiled code, interpreted code, machine code, executable instructions, and/or the like may be used to control certain aspects of the operation of the computing entity 200 with the assistance of the processing element 205 and operating system.

As indicated, in one embodiment, the computing entity 200 may also include one or more network and/or communications interfaces 220 for communicating with various computing entities, such as by communicating data, content, information, and/or similar terms used herein interchangeably that can be transmitted, received, operated on, processed, displayed, stored, and/or the like. For instance, the computing entity 200 may communicate with computing entities or communication interfaces of other computing entities 200, user computing entities 30, and/or the like.

As indicated, in one embodiment, the computing entity 200 may also include one or more network and/or communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the computing entity 200 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1X (1xRTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra wideband (UWB), infrared (IR) protocols, near field communication (NFC) protocols, Wibree, Bluetooth protocols, wireless universal serial bus (USB) protocols, and/or any other wireless protocol. The computing entity 200 may use such protocols and standards to communicate using Border Gateway Protocol (BGP), Dynamic Host Configuration Protocol (DHCP), Domain Name System (DNS), File Transfer Protocol (FTP), Hypertext Transfer Protocol (HTTP), HTTP over TLS/SSL/Secure, Internet Message Access Protocol (IMAP), Network Time Protocol (NTP), Simple Mail Transfer Protocol (SMTP), Telnet, Transport Layer Security (TLS), Secure Sockets Layer (SSL), Internet Protocol (IP), Transmission Control Protocol (TCP), User Datagram Protocol (UDP), Datagram Congestion Control Protocol (DCCP), Stream Control Transmission Protocol (SCTP), HyperText Markup Language (HTML), and/or the like.

As will be appreciated, one or more of the computing entity's 200 components may be located remotely from other computing entity 200 components, such as in a distributed system. Furthermore, one or more of the components may be aggregated and additional components performing functions described herein may be included in the computing entity 200. Thus, the computing entity 200 can be adapted to accommodate a variety of needs and circumstances.

b. Exemplary User Computing Entity

Figure 3:
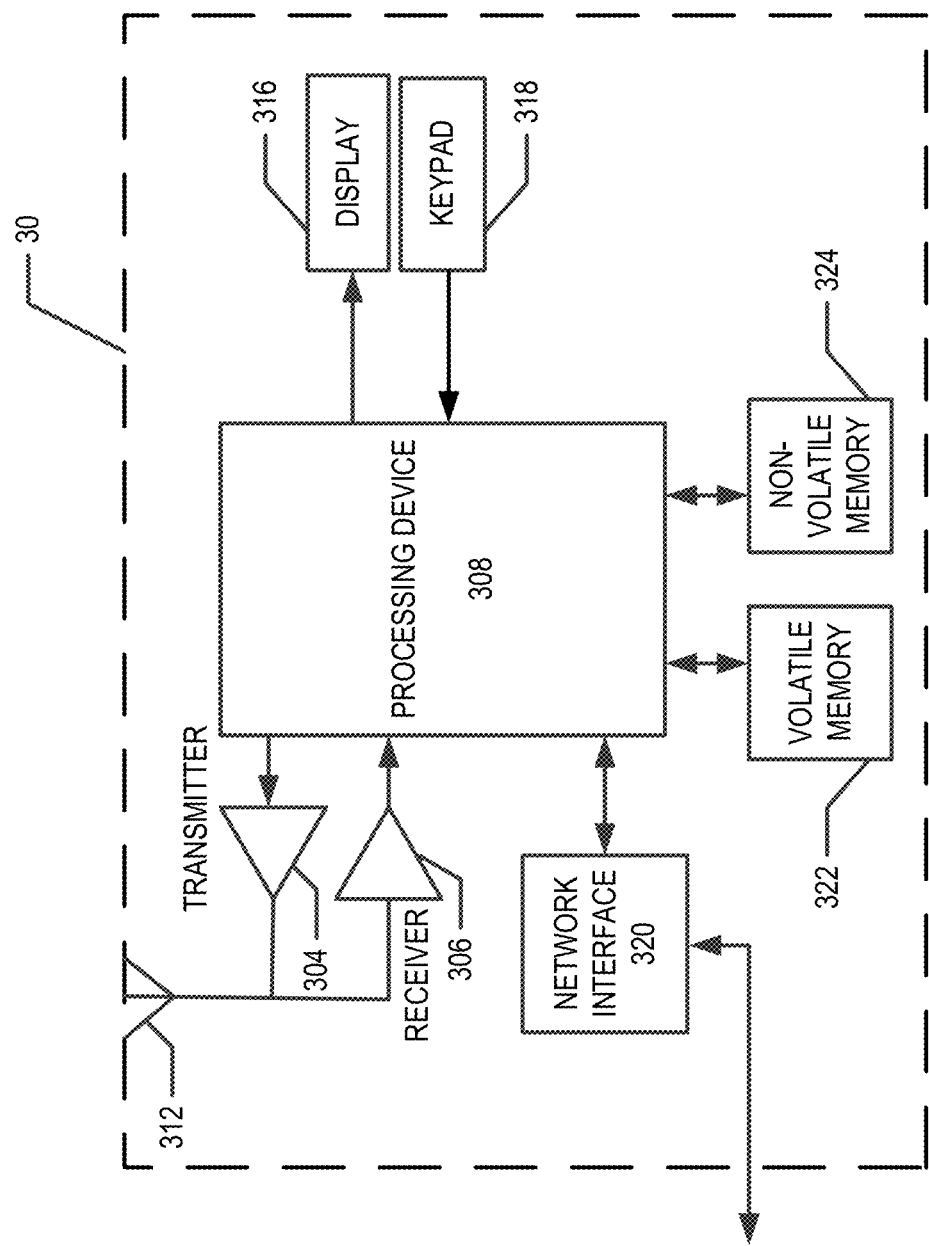
FIG. 3 is a schematic of a user computing entity in accordance with certain embodiments of the present invention.

FIG. 3 provides an illustrative schematic representative of user computing entity 30 that can be used in conjunction with embodiments of the present invention. As shown in FIG. 3, a user computing entity 30 can include an antenna 312, a transmitter 304 (e.g., radio), a receiver 306 (e.g., radio), and a processing element 308 that provides signals to and receives signals from the transmitter 304 and receiver 306, respectively. The signals provided to and received from the transmitter 304 and the receiver 306, respectively, may include signaling information/data in accordance with an air interface standard of applicable wireless systems to communicate with various entities, such as a computing entity 200, another user computing entity 30, and/or the like. In this regard, the user computing entity 30 may be capable of operating with one or more air interface standards, communication protocols, modulation types, and access types. More particularly, the user computing entity 30 may operate in accordance with any of a number of wireless communication standards and protocols. In a particular embodiment, the user computing device 30 may operate in accordance with multiple wireless communication standards and protocols, such as GPRS, UMTS, CDMA2000, 1xRTT, WCDMA, TD-SCDMA, LTE, E-UTRAN, EVDO, HSPA, HSDPA, Wi-Fi, WiMAX, UWB, IR protocols, Bluetooth protocols, USB protocols, and/or any other wireless protocol.

Via these communication standards and protocols, the user computing entity 30 can communicate with various other entities using concepts such as Unstructured Supplementary Service information/data (USSD), Short Message Service (SMS), Multimedia Messaging Service (MMS), Dual-Tone Multi-Frequency Signaling (DTMF), and/or Subscriber Identity Module Dialer (SIM dialer). The user computing entity 30 can also download changes, add-ons, and updates, for instance, to its firmware, software (e.g., including executable instructions, applications, program modules), and operating system.

According to one embodiment, the user computing entity 30 may include location determining aspects, devices, modules, functionalities, and/or similar words used herein interchangeably. For example, the user computing entity 30 may include outdoor positioning aspects, such as a location module adapted to acquire, for example, latitude, longitude, altitude, geocode, course, direction, heading, speed, UTC, date, and/or various other information/data. In one embodiment, the location module can acquire data, sometimes known as ephemeris data, by identifying the number of satellites in view and the relative positions of those satellites. The satellites may be a variety of different satellites, including LEO satellite systems, DOD satellite systems, the European Union Galileo positioning systems, the Chinese Compass navigation systems, Indian Regional Navigational satellite systems, and/or the like. Alternatively, the location information/data may be determined by triangulating the computing entity's 200' position in connection with a variety of other systems, including cellular towers, Wi-Fi access points, and/or the like. Similarly, the user computing entity 30 may include indoor positioning aspects, such as a location module adapted to acquire, for example, latitude, longitude, altitude, geocode, course, direction, heading, speed, time, date, and/or various other information/data. Some of the indoor aspects may use various position or location technologies including RFID tags, indoor beacons or transmitters, Wi-Fi access points, cellular towers, nearby computing devices (e.g., smartphones, laptops) and/or the like. For instance, such technologies may include iBeacons, Gimbal proximity beacons, BLE transmitters, Near Field Communication (NFC) transmitters, and/or the like. These indoor positioning aspects can be used in a variety of settings to determine the location of someone or something to within inches or centimeters.

The user computing entity 30 may also comprise a user interface device comprising one or more user input/output interfaces (e.g., a display 316 and/or speaker/speaker driver coupled to a processing element 308 and a touch screen, keyboard, mouse, and/or microphone coupled to a processing element 308). For example, the user output interface may be configured to provide an application, browser, interactive user interface, dashboard, webpage, and/or similar words used herein interchangeably executing on and/or accessible via the user computing entity 30 to cause display or audible presentation of information/data and for user interaction therewith via one or more user input interfaces. The user input interface can comprise any of a number of devices allowing the user computing entity 30 to receive data, such as a keypad 318 (hard or soft), a touch display, voice/speech or motion interfaces, scanners, readers, or other input device. In embodiments including a keypad 318, the keypad 318 can include (or cause display of) the conventional numeric (0-9) and related keys (#, *), and other keys used for operating the user computing entity 30 and may include a full set of alphabetic keys or set of keys that may be activated to provide a full set of alphanumeric keys. In addition to providing input, the user input interface can be used, for example, to activate or deactivate certain functions, such as screen savers and/or sleep modes. Through such inputs the user computing entity 30 can collect information/data, user interaction/input, and/or the like.

The user computing entity 30 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, RRAM, SONOS, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, RIMM, DIMM, SIMM, VRAM, cache memory, register memory, and/or the like. The volatile and non-volatile storage or memory can store databases, database instances, database management system entities, data, applications, programs, program modules, scripts, source code, object code, byte code, compiled code, interpreted code, machine code, executable instructions, and/or the like to implement the functions of the user computing entity 30.

c. Exemplary Networks

In one embodiment, any two or more of the illustrative components of the architecture of FIG. 1 may be configured to communicate with one another via respective communicative couplings to one or more networks 135. The networks 135 may include, but are not limited to, any one or a combination of different types of suitable communications networks such as, for example, cable networks, public networks (e.g., the Internet), private networks (e.g., frame-relay networks), wireless networks, cellular networks, telephone networks (e.g., a public switched telephone network), or any other suitable private and/or public networks. Further, the networks 135 may have any suitable communication range associated therewith and may include, for example, global networks (e.g., the Internet), MANs, WANs, LANs, or PANs. In addition, the networks 135 may include any type of medium over which network traffic may be carried including, but not limited to, coaxial cable, twisted-pair wire, optical fiber, a hybrid fiber coaxial (HFC) medium, microwave terrestrial transceivers, radio frequency communication mediums, satellite communication mediums, or any combination thereof, as well as a variety of network devices and computing platforms provided by network providers or other entities.

IV. Exemplary System Operation

Medical information/data (and similar words used herein interchangeably) is often encoded using medical codes. For example, procedure codes, diagnostic codes, prescription or drug codes, equipment codes, revenue codes, place of service codes, and/or the like may be used to encode various portions of an instance of medical information/data. The encoding of the medical information/data using medical codes may be manually performed by a trained professional. For example, various colleges and universities offer certificate programs that train people to perform the encoding of the medical information/data into medical codes. Given the medical knowledge required to make sense of medical information/data encoded using medical codes, automated and/or computerized analysis of encoded medical information/data generally fails to capture the complexity and/or full picture provided by the encoded medical information/data. Moreover, computer analysis of medical information/data encoded in medical codes cannot be effectively performed using the same methodology of analyzing textual information. For example, grammar rules may be used to aid the analysis of textual information, but medical codes are not subject to any such grammar rules.

Various embodiments of the present invention provide a technical solution to these technical problems by transforming medical codes into digital representations of patients that encode the patients' medical histories. In an example embodiment, a digital representation of a patient is a multi-dimensional vector in a multi-dimensional space. For example, the digital representation of the patient may be a list or array of numbers that encodes the patient's medical history. For example, a vector generation model may be trained using machine learning such that the vector generation model may generate a vector dictionary and/or one or more digital representations of patients. The vector dictionary may link one or more medical codes to corresponding multi-dimensional vectors. The multi-dimensional vectors may be generated such that a first medical code and a second medical code that are closely related may be assigned and/or may correspond to multi-dimensional vectors that have a smaller distance or smaller angle there between in the multi-dimensional space than a third medical code and a fourth medical code that are not closely related. For example, current procedural terminology (CPT) code J9002, corresponding to doxorubicin administration, may correspond to a multi-dimensional vector that is closer to the multi-dimensional vector corresponding to diagnosis code C50.919, corresponding to breast cancer, than to the multi-dimensional vector corresponding to CPT code J0133, corresponding to injectable acyclovir. As should be understood, in this context, the term "closer" refers to a shorter distance or a smaller angle between the multi-dimensional vectors in the multi-dimensional space. Thus, the medical knowledge regarding the relationships between various codes may be encoded through the correspondence of medical codes with multi-dimensional vectors, as in the vector dictionary. Moreover, the vector dictionary may define one or more anagram relationships between various medical codes. An example anagram relationship between first, second, and third multi-dimensional vectors may be that the combination of a first multi-dimensional vector corresponding to a medical code indicating high cholesterol and a second multi-dimensional vector corresponding to a medical code indicating hypertension may result in a multi-dimensional vector that is equal to and/or within a threshold value of a third multi-dimensional vector corresponding to a medical code corresponding to type 2 diabetes. In various embodiments, an anagram relationship between a set of multi-dimensional vectors indicates that the combination of two or more of the multi-dimensional vectors of the set results in another of multi-dimensional vectors of the set and/or a combination of two or more other multi-dimensional vectors in the set.

In an example embodiment, the digital representation of a patient corresponds to a health state for the patient. For example, various regions of the multi-dimensional space may be associated with unhealthiness and other various regions of the multi-dimensional space may be associated with healthiness. Thus, if a digital representation of a patient is a vector located within a region associated with unhealthiness, it may be desirable to determine what future actions, medical decisions, and/or the like may cause the vector to move towards and/or into a region of the multi-dimensional space associated with healthiness. In various embodiments, the digital representation and the vector dictionary and/or a digital representation of a cohort of patients with medical histories that are similar to the patients may be used to determine a possible future health state of the patient.

Generating and Providing a Digital Representation and/or Current Health State of a First Patient FIG. 4 provides a flowchart illustrating processes, procedures, and/or operations for generating and providing a digital representation of a first patient of a population of patients. Starting at step/operation 402, a plurality of instances of medical information/data is accessed. For example, the computing entity 200 may access a plurality of instances of medical information/data. In an example embodiment, the plurality of instances of medical information/data (or at least a portion thereof) are stored in a database or other data store by the computing entity 200. In an example embodiment, the plurality of instances of medical information/data (or at least a portion thereof) are accessed by providing a request for medical information/data to another computing entity 200 (e.g., via the communication interface 220) or data store and receiving the instances of medical information/data (e.g., via the communication interface 220) in response to the request. In an example embodiment, the request could identify one or more patients or for which medical information/data is being requested. In an example embodiment, each instance of medical information/data may be associated with and/or comprise a patient identifier, a timestamp comprising a date and/or time corresponding to the one or more medical codes of the instance of medical information/data, one or more medical codes (e.g., diagnosis, procedure, prescription or drug, equipment and/or other medical codes), geographical information corresponding to the location of the particular visit (e.g., the street address, city, state, and/or the like where the particular patient visit occurred), demographic information/data corresponding to the patient, and/or other information/data relevant to the instance of medical information/data (e.g., physicians notes, and/or other textual components of medical information/data, and/or the like).

In various embodiments, the plurality of instances of medical information/data provide at least a significant portion of the medical history of each of a population of patients. In an example embodiment, a population of patients comprises a plurality of patients. In various embodiments, a significant portion of a patient's medical history comprises major medical events in the patient's life; medical information/data corresponding to the totality of the patient's life; medical information/data corresponding to the totality of a patient's adult life; medical information/data for the patient from the preceding twenty years, fifteen years, ten years, five years, two years, one year; and/or the like. In an example embodiment, the plurality of instances of medical information/data comprises a similar portion of the medical history of each patient of the population of patients. In an example embodiment, an instance of medical information/data corresponds to a particular patient visit, a day in hospital, or collection of visits/days in a week/month or other time range, and/or the like. The plurality of instances may consist of medical information/data from a payer, a government entity (VA, state Medicare claims), a registry of patients with a specific disease or treatment; a collection of medical records, and/or the like.

At step/operation 404, a plurality of medical sentences are generated from the plurality of instances of medical information/data. For example, the computing entity 200 may generate a plurality of medical sentences from the plurality of instances of medical information/data. In an example embodiment, a medical sentence is a string of the medical codes (e.g., procedure codes, diagnosis codes, prescription or drug codes, equipment codes, revenue codes, place of service codes, and/or the like) corresponding to a particular patient. In an example embodiment, the medical codes used to generate the medical sentence may also comprise one or more words such as a drug name, procedure name, diagnosis name, and/or the like as long as the words and/or medical codes are consistent across the plurality of instances of medical information/data. As used herein, the term medical codes includes these words that are applied consistently across the plurality of instances of medical information/data, in an example embodiment.

In various embodiments, one medical sentence is generated for each patient in the population of patients. For example, a plurality of medical sentences may be generated with each medical sentence corresponding to a particular patient of the population of patients. The medical codes of the medical sentence corresponding to a patient are ordered by when the medical events occurred. For example, all of the instances of medical information/data corresponding to a first patient are identified by identifying the instances of medical information/data corresponding to and/or comprising the patient identifier identifying the first patient. The medical sentence for the first patient is then generated by ordering the medical codes based on chronological order using the timestamps of the instances of medical information/data.

In an example embodiment, the medical sentence corresponding to the first patient may be filtered. In an example embodiment, the medical sentence corresponding to the patient identifier configured to identify the first patient (e.g., generated based on instances of medical information/data corresponding to the same patient/patient identifier) may be filtered to only include the first instance of each medical code and/or each diagnosis code. For example, if the first patient is diagnosed with high cholesterol, multiple instances of medical information/data corresponding to the first patient may comprise the diagnosis code for high cholesterol. The medical sentence corresponding to the first patient may then be filtered to remove any repeated/duplicate diagnosis codes for high cholesterol. In another example embodiment, the medical sentence corresponding to a patient identifier configured to identify the first patient may be filtered to remove repeated/duplicate prescription/drug codes. For example, if a patient is prescribed a long term and/or maintenance drug (e.g., a statin) a plurality of instances of medical information/data may include the prescription/drug code corresponding to the long term and/or maintenance drug. The medical sentence corresponding to the first patient may then be filtered to remove all but the first instance of the prescription/drug code. For example, if a patient gets a refill for her statin and picks up an antibiotic prescription for a sinus infection at the same time, an instance of medical information/data may include both the prescription/drug code corresponding to the statin and the prescription/drug code corresponding to the antibiotic. To prevent the vector generation model from learning a false connection between the prescription/drug code corresponding to the statin and the prescription/drug code corresponding to the antibiotic, only the first instance of prescription/drug code corresponding to the statin may be included in the set of medical sentences corresponding to the patient identifier configured to identify the first patient. In various embodiments, this filtering may be executed between the steps of accessing the medical information/data and generating the medical sentences.

In various embodiments, each of the medical sentences may be of the same length. For example, each of the medical sentences for the patients of the population of patients may comprise a particular number of medical codes. In an example embodiment, after the medical sentences have been generated based on the plurality of instances of medical information/data, the longest medical sentence may be identified. For example, the medical sentence having the largest number of medical codes therein may be identified based on its length. The number of medical codes of the longest medical sentence is then set as the particular number. The remainder of the medical sentences are then padded with one or more dummy codes such that each of the plurality of medical sentences comprises the particular number of medical codes. For example, one or more dummy codes may be added to one or more medical sentences so that each medical sentence of the plurality of medical sentences comprises the particular number of medical codes. In an example embodiment, a dummy code may be an alphanumeric code that is added to a medical sentence to make the medical sentence longer but that does not affect the health state indicated by the resulting digital representation of the patient corresponding to the medical sentence.

In an example embodiment, a medical sentence, in addition to including the particular number of medical codes, comprises and/or is associated with metadata including a patient identifier. In an example embodiment, a medical sentence may be annotated with a timestamp for each medical code. In an example embodiment, a medical sentence is annotated with the time distance between adjacent and/or neighboring medical codes of the medical sentence. For example, a medical sentence may comprise annotations, meta data, and/or the like indicating that an event corresponding to the first medical code and an event corresponding to an adjacent and/or neighboring second medical code occurred on the same day and that the event corresponding to the second medical code and an event corresponding to an adjacent and/or neighboring third medical code occurred two years apart (e.g., the event corresponding to the third medical code occurred two years after the event corresponding to the second medical code occurred). In various embodiments, the vector generation model may be configured to encode the medical sentence into a digital representation that considers the temporal relationships between the medical codes of the medical sentence.

At step/operation 406, the vector generation model may be trained. For example, the computing entity 200 may train the vector generation model using machine learning. For example, at least some of the plurality of medical sentences may be used as a training data set to train the vector generation model using machine learning. In an example embodiment, the vector generation model is trained using unsupervised machine learning. In various embodiments, the vector generation model may be a modified fastText, word2vec, GloVe, or other algorithm. In a particular example, the vector generation model may be an embedding layer of a deep net, neural network, and/or the like.

In an example embodiment, the vector generation model is trained to transfer, link, associate, and/or the like a medical code to a multi-dimensional vector in a multi-dimensional space. In an example embodiment, the dimensionality of the multi-dimensional space may be predetermined, predefined, and/or configurable. In an example embodiment, the dimensionality of the multi-dimensional space may be determined based on user input. In an example embodiment, the dimensionality of the space may be determined based on an automatic determination and/or estimate of the number of dimensions required to fully encode the medical codes within the multi-dimensional space. In an example embodiment, the number of dimensions of the multi-dimensional space is in the inclusive range of 50 to 100 dimensions. In an example embodiment, the number of dimensions of the multi-dimensional space is in the inclusive range of 10 to 1000 dimensions. In various embodiments, the dimensions themselves do not have semantic meaning. Rather, the distances or angles between the multi-dimensional vectors within the multi-dimensional space provide semantic meaning to the model. For example, the vector generation model may be trained using machine learning to assign, link, and/or associate a multi-dimensional vector to each of a plurality of medical codes based on the inter-relatedness of the medical codes such that the distance or angle between two multi-dimensional vectors within the multi-dimensional space indicates how closely and/or strongly related the two corresponding medical codes are.

In an example embodiment, the vector generation model may be trained through the analysis of the one or more medical sentences of the plurality of medical sentences using a code window. In various embodiments, the code window may be predetermined, predefined, or configurable.

In an example embodiment, the code window is in the inclusive range of two to ten codes. In a particular example, the code window may be predetermined to be three codes wide. In an example embodiment, the code window is predetermined to be five codes wide. In an example embodiment, the code window is a rolling code window. The vector generation model may interpret codes that appear within the code window at the same time as being related. For example, FIG. 5 illustrates five code wide window 504 rolling a medical sentence 502 comprising a plurality of medical codes 506. The medical sentence 502 may be analyzed using code window 504 that is five codes wide, as shown by the thick lines. Medical codes 506 that appear within the same code window 504 may be considered to be related. For example, medical code pairs E669 and B349, E669 and K760, B349 and E669, B349 and K760, B439 and R109, K760 and E669, K760 and B349, K760 and R109, K760 and R109, R109 and B349, R109 and K760, R109 and R109, and R109 and Hydrocodone may be considered related. However, based on the portion of the medical sentence 502 shown in FIG. 5 and the five code wide code window 504, E669 and Hydrocodone are not considered related, for example. In training the vector generation model, the number of times two medical codes appear within the same code window 504 throughout the analysis of the set of medical sentences, the stronger the relationship between the two medical codes is interpreted to be. For example, medical codes E669 and K760 may be considered more strongly related than medical codes E669 and R109. Thus, the vector generation model may link and/or associate the medical codes E669 and K760 to multi-dimensional vectors within the multi-dimensional space that are closer in distance and/or angle (within the multi-dimensional space) than the multi-dimensional vectors linked and/or associated to the medical codes E669 and R109. For example, the multi-dimensional vectors linked and/or assigned to medical codes E669 and K760 may be separated by less distance or a smaller angle within the multi-dimensional space than the multi-dimensional vectors linked and/or assigned to medical codes E669 and R109.

FIG. 6 illustrates a schematic diagram of an example vector generation model 600. The vector generation model 600 is configured to receive one or input vectors 602 each representing a medical sentence of the plurality of medical sentences corresponding to the population of patients at the input layer 604. The input layer 604 passes the input vector 602 to one or more hidden layers 606. In various embodiments, the hidden layers 606 are classifier layers, encoder layers, and/or the like. The one or more hidden layers 606 provide results to the output layer 608. In an example embodiment, the output layer 608 is a classifier layer. For example, the output layer 608 may be a softmax classifier. In an example embodiment, the output layer 608 comprises as many nodes as the number of vocabulary items (e.g., unique medical codes) in the plurality of medical sentences.

Continuing with FIG. 4, at step/operation 408, a vector dictionary is generated. For example, the computing entity 200 may use the vector generation model to generate a vector dictionary. The vector dictionary may be stored in memory 210, 215. In an example embodiment, the vector dictionary comprises a set of medical codes and the corresponding, linked, and/or assigned multi-dimensional vectors. For example, the vector dictionary may comprise a multi-dimensional vector corresponding, linked, and/or assigned to each vocabulary item (e.g., unique medical code) of the plurality of medical sentences. For example, the vector dictionary may indicate the multi-dimensional vector corresponding, linked, and/or assigned to each medical code of a plurality of medical codes. The multi-dimensional vectors assigned, linked, and/or corresponding to each of the medical codes may encode the relationships and/or strength of the relationships between pairs and/or groups of medical codes. In particular, the relative distance and/or angle within the multi-dimensional space between a first pair of multi-dimensional vectors corresponding to a first pair of medical codes and a second pair of multi-dimensional vectors corresponding to a second pair of medical codes may indicate the relative relatedness and/or strength of the relationships between the corresponding medical codes. In various embodiments, the computing entity stores the vector dictionary (e.g., memory 210, 215) for future use and/or reference. In an example embodiment, the computing entity 200 may analyze the vector dictionary to identify any anagram relationships corresponding to multi-dimensional vectors of the vector dictionary. In an example embodiment, information/data describing the identified anagram relationships may be stored as part of the vector dictionary.

At step/operation 410, a digital representation of a first patient is generated. In an example embodiment, the first patient is one of the plurality of patients of the population of patients. In an example embodiment, the computing entity 200 uses the vector generation model 600 to generate a digital representation of the first patient. In an example embodiment, the computing entity 200 accesses the vector dictionary and uses the vector dictionary to combine a plurality of multi-dimensional vectors corresponding to the medical codes of the medical sentence representing the medical history of the first patient to generate the digital representation of the first patient. In various embodiments, the digital representation of the first patient may be a list or array of numbers or a multi-dimensional vector within a multi-dimensional space. In an example embodiment, the digital representation of the first patient is of a fixed length. For example, the multi-dimensional vector of the digital representation of the first patient may have a fixed length such that the digital representation of each patient of the population of patients is the same length. In an example embodiment, the length of the multi-dimensional vector of the digital representation is a multi-dimensional generalization of Euclidean length.

In an example embodiment, the combining of the multi-dimensional vectors may be performed using a predefined combining function. In an example embodiment, the combining function used to combine multi-dimensional vectors (e.g., from the vector dictionary) may be vector addition. In an example embodiment, the combining function used to combine multi-dimensional vectors (e.g., from the vector dictionary) may be a function that takes the chronology of the events corresponding to the medical codes into account. For example, if an event corresponding to medical code A occurred on Monday and an event corresponding to medical code B occurred on Wednesday, the resulting digital representation of the corresponding patient may be different that if the event corresponding to medical code B occurred on Monday and the event corresponding to medical code A occurred on Wednesday. In an example embodiment, the digital representation corresponding to a medical sentence wherein the event corresponding to medical code A occurred on Monday and the event corresponding to medical code B occurred on Wednesday is different from the digital representation corresponding to a medical sentence wherein the event corresponding to medical code A occurred on Monday and the event corresponding to medical code B occurred on Tuesday. Thus, in an example embodiment, the combining function used to combine the multi-dimensional vectors to generate a digital representation of the first patient (e.g., based on the vector dictionary) may depend on the order of medical codes within the medical sentence and/or the amount of time that has elapsed between events corresponding to adjacent and/or neighboring medical codes within the medical sentence.

In various embodiments, the digital representation of the first patient may indicate a health state of the first patient. For example, various regions of the multi-dimensional space may be associated with healthful states and various other regions of the multi-dimensional space may be associated with unhealthful states. For example, FIG. 7A illustrates an example two-dimensional space 700 having defined thereon unhealthful regions 704 corresponding to unhealthy states and healthful regions 702 corresponding to healthy states. In various embodiments, the multi-dimensional space may have a health topology defined thereon such that at each point in the multi-dimensional space, a health state is associated therewith. For example, FIG. 7B illustrates an example two-dimensional space 750 having health contours 752 defining and/or illustrating a health topology on the space. For example, patient A having a digital representation A may be in a less healthy state than patient B having a digital representation B, and patient B may be in a less healthy state than patient C having a digital representation C. In an example embodiment, patients B and C may be simulated future versions of patient A. Thus, various embodiments, may assist a patient in understand how best to improve his or her health state. In an example embodiment, the regions of the multi-dimensional space associated with healthful states and the regions of the multi-dimensional space associated with unhealthful states and/or the health topology of the multi-dimensional space may be determined and/or defined by the vector generation model. In an example embodiment, the regions of the multi-dimensional space associated with healthful states and the regions of the multi-dimensional space associated with unhealthful states and/or the health topology of the multi-dimensional space may be determined and/or defined by a human operator via an interactive user interface of the computing entity 200 and/or user computing entity 30.

In an example embodiment, a past or possible future digital representation of the first patient is generated. For example, one or more medical codes of the medical sentence corresponding to the patient's medical history may be replaced with dummy codes and/or one or more dummy codes of the medical sentence corresponding to the first patient may be replaced with medical codes corresponding to therapies, prescriptions, diagnosis and/or the like that are expected to be relevant to the first patient's medical history at a future point in time. Thus, a digital representation corresponding to a past health state of the patient and/or a possible future health state of the patient may be generated.

In various embodiments, the computing entity 200 is configured to provide the digital representation of the first patient. For example, the computing entity 200 may provide the digital representation of the first patient as input to a simulation and/or the like for determining a possible future health state for the first patient and/or the like. In an example embodiment, the digital representation of the first patient may be provided for display via a user interface of the computing entity 200 and/or a user computing entity 30. For example, a visualization of the digital representation of the first user and/or the first user's current health state (as indicated by the digital representation of the first user) may be provided (e.g., transmitted) such that the user computing entity 30 receives the visualization, processes the visualization, and causes the visualization to be displayed via the display 316 of the user computing entity 30 for user interaction therewith. In an example embodiment, the computing entity 200 may store the digital representation of the first patient in a patient representation database (e.g., in memory 210, 215) and/or the like. In various embodiments, a digital representation of the first patient may be generated and/or determined for the current state of the first patient, for past states of the first patient (e.g., a digital representation of the first patient five years ago based on the medical history of the first patient up to a date five years ago, and/or the like), and/or for future states of the first patient (e.g., by adding a hypothetical future medical history for the first patient).

In various embodiments, a sentence generation model is trained after the training of the vector generation model and/or in parallel therewith. The sentence generation model is configured to receive a digital representation of a patient (e.g., as determined and/or generated by the vector generation model) and determine a medical sentence for the patient. In an example embodiment, a medical sentence uniquely defines a digital representation such that two different (even if similar) medical sentences will not result in the same digital representation. The sentence generation model is configured to receive a digital representation and determine and/or generate the unique medical sentence that resulted in the corresponding digital representation.

Generating and Providing a Possible Future Health State of the First Patient

FIG. 8 provides a flowchart illustrating example procedures, processes, and/or operations performed by a computing entity to determine a possible future health state for a first patient, in accordance with an example embodiment of the present invention. In various embodiments, the possible future health state of the first patient is an optimal health state of the first patient given the first patient's medical history, an expected future health state determined based on digital representations of a cohort of patients having similar medical histories as the first patient, a predicted result of a medical decision for the first patient, and/or the like. In various embodiments, the possible future health state is determined using an anagram model. In an example embodiment, using an anagram model comprises combining the digital representation of the first patient with one or more multi-dimensional vectors from the vector dictionary to simulate the possible future health state of the first patient and/or applying one or more anagram relationships identified within the vector dictionary to the digital representation of the first patient. In various embodiments, an anagram relationship between a set of multi-dimensional vectors indicates that the combination of two or more of the multi-dimensional vectors of the set results in another multi-dimensional vector of the set and/or a combination of two or more other multi-dimensional vectors in the set. In various embodiments, anagram relationships between various multi-dimensional vectors of the vector library may be determined prior to determining the possible future health state for the first patient. In an example embodiment, applying an anagram relationship to the digital representation of the first patient includes determining a code that is likely and/or expected to be associated with the patient's medical records (either currently or at some point in the future) based on the anagram relationship.

Starting at step/operation 802, the digital representation of the first patient and the vector dictionary are accessed. For example, the computing entity 200 may access the digital representation of the first patient from cache and/or from a patient representation database stored in memory 210, 215. For example, the computing entity 200 may access the vector dictionary from cache and/or from the memory 210, 215.

At step/operation 804, a cohort of second patients that have similar medical histories to the first patient are identified. For example, the computing entity 200 may identify a cohort of second patients that have similar medical histories to the first patient. For example, a second patient may be said to have a similar medical history to the first patient if the vector corresponding to a digital representation of the second patient satisfies a predefined distance threshold requirement with respect to the vector corresponding to the first patient within the multi-dimensional space. For example, if the vector corresponding to the second patient is within a threshold distance within the multi-dimensional space of the vector corresponding to the first patient, the second patient has a similar medical history as the first patient and the second patient is considered to be part of the cohort of second patients that have similar medical histories to the first patient. In various embodiments, the distance within the multi-dimensional space may be Euclidean distance, cosine distance, and/or other distance measure within the multi-dimensional space. For example, in an example embodiment the distance between vectors in the multi-dimensional space is an angle or value indicative of an angle (e.g., cosine distance).

In an example embodiment, a second patient may be said to have a similar medical history to the first patient if the vector corresponding to a digital representation of the second patient satisfies a population percentage threshold requirement with respect to the vector corresponding to the first patient within the multi-dimensional space. For example, if the distance within the multi-dimensional space between the vector corresponding to the second patient and the vector corresponding to the first patient is smaller and/or less than the distance between a vector corresponding to a predefined percentage of the population of patients and the vector corresponding to the first patient, the second patient has a similar medical history as the first patient and the second patient is considered to be part of the cohort of second patients that have similar medical histories to the first patient. In various embodiments, the predefined percentage may be 98%, 95%, 90%, 85%, 80%, 75%, 70%, and/or the like as appropriate for the application and/or population of patients. For example, if the population of patients is a population of patients with a particular disease, the criteria for identifying a cohort of second patients may be stricter than if the population of patients is a random selection of patients.

In another example, if the distance within the multi-dimensional space between the vector corresponding to the second patient and the vector corresponding to the first patient is smaller and/or less than a predetermined multiple of the standard deviation less than the average (e.g., mean) distance between the vector corresponding to the first patient and a vector corresponding to another patient within the population of patients, the second patient is considered to be a member of the cohort of second patients having similar medical histories as the first patient and is considered to have a similar medical history to the first patient. For example, the predetermined multiple of the standard deviation may, in various embodiments, be one and a half standard deviations, two standard deviations, two and a half standard deviations, three standard deviations, and/or the like as appropriate for the application and/or population of patients.

At step/operation 806, an anagram model may be used to determine, generate, and/or define a possible future health state of the first patient. For example, the computing entity 200 may determine, generate, and/or define a possible future health state of the first patient. In various embodiments, the possible future health state of the first patient is an optimal health state of the first patient given the first patient's medical history, an expected future health state determined based on digital representations of a cohort of second patients having similar medical histories as the first patient, or a predicted result of a medical decision for the first patient. For example, it may be determined what the healthiest possible future health state of the first patient is given the starting point of the first patient's medical history. For example, to determine the optimal health state of the first patient, one or more multi-dimensional vectors may be added to the vector corresponding to the digital representation of the first patient to determine whether the digital representation may be moved from an unhealthy region to a healthy region and/or to a healthier state than the current location of the vector. For example, the medical codes corresponding to multi-dimensional vectors that, when added to the vector corresponding to the digital representation of the first patient, move the vector corresponding to the digital representation toward a heathy region and/or toward a healthier state may be determined and/or identified such that they may be provided (e.g., such that they are received by a user computing entity 30 for display/provision via an interactive user interface of the user computing entity 30). In an example, embodiment, the optimal health state for the first patient, given the medical history of the first patient as represented by the digital representation of the first patient, may then be the resulting healthiest possible future health state for the first patient. The one or more medical codes corresponding to the multi-dimensional vector(s) combined with the vector corresponding to the digital representation of the first patient may be stored such that they may be provided (e.g., such that they are received by a user computing entity 30 for display/provision via an interactive user interface of the user computing entity 30).

In an example embodiment, an expected future health state for the first patient may be determined based on the digital representation of the first patient and the digital representations of a cohort of second patients that have similar medical histories to the first patient. For example, based on the cohort of second patients, it may be determined what the next significant medical event for the first patient will be. For example, it may be determined which multi-dimensional vectors and the corresponding medical codes from the vector dictionary would bring the vector corresponding to the first patient into alignment (e.g., within the predefined threshold distance) with the average (e.g., mean, median, and/or mode) of the vectors corresponding to the second patients of the cohort. For example, it may be determined that when a multi-dimensional vector corresponding to a first medical code is combined (e.g., using the predefined combining function) with the vector corresponding to the digital representation of the first patient, the resulting vector is within a predefined threshold distance of the average of the vectors corresponding to the digital representation of the second patients of the cohort. The medical event corresponding to the first medical code may be stored and/or provided (e.g., such that they are received by a user computing entity 30 for display/provision via an interactive user interface of the user computing entity 30) as an expected future health state of the first patient. Various other techniques may be used to determine an expected future health state of the first patient based on the digital representation of the first patient and the cohort of second patients in various embodiments.

In an example embodiment, a predicted result of a medical decision for the first patient may be determined and/or generated. For example, one or more multi-dimensional vectors corresponding to one or more medical codes may be combined with the vector corresponding to the digital representation of the first patient to determine an outcome of a medical decision. For example, a physician may be considering providing a particular prescription to the first patient. By combining a multi-dimensional vector corresponding to the particular prescription to the vector corresponding to the digital representation of the first patient, a prediction of whether the prescription will move the digital representation of the first patient toward a healthier state may be determined. Expected and/or predicted results of various other medical decisions, in addition to prescriptions, may be determined in a similar manner (e.g., by combining appropriate multi-dimensional vectors of the vector dictionary to the vector corresponding to the digital representation of the first patient).

At step/operation 808, an output is provided. For example, the computing entity 200 may provide an output identifying the first patient, the possible future health state of the first patient, one or more identified medical codes (and/or medical terms corresponding to the one or more identified medical codes used to transform the current health state of the first patient to the possible future health state, information/data regarding and/or determined based on the cohort of second patients, and/or the like. In an example embodiment, the computing entity 200 may provide the output via an output device of the computing entity 200 (e.g., a display device, a user interface, an audio output, cause a printer to print the output, and/or the like). In an example embodiment, the output is provided as input to another application and/or program operating on the computing entity 200. In an example embodiment, the computing entity 200 may provide (e.g., transmit) the output via a network interface 220. For example, the user computing entity 30 may receive the output (e.g., via network interface 320 or receiver 306) and cause display of at least a portion of the output via display 316, and/or the like via an interactive user interface.

As noted above, this output may be used to determine a best course of action for treating the first patient, a plan for improving the first patient's health state, predicting a future health state of the first patient, and/or the like. In an example embodiment, the computing entity 200 may be configured to train (e.g., via machine learning) and/or use predictive models that are based on digital representations corresponding to patients. For example, a predictive model may be used to predict the occurrence of a clinical event for the first patient based on the corresponding digital representation, the cohort of second patients, and/or the like. For example, the predictive model may be trained using machine learning with a training data set comprising a plurality of digital representations that each correspond to a second patient of the cohort of second patients. After the predictive model is trained, a digital representation of a first patient may be provided and the predictive model may provide a likelihood that the first patient will experience one or more clinical events. In an example embodiment, the likelihood that the first patient will experience the one or more clinical events corresponds to a predetermined, predefined, configurable, or other time period. In an example embodiment, an output of the predicative model (e.g., the likelihood the first patient will experience one or more clinical events) will be provided such that the user computing entity 30 receives the output and provides at least a portion thereof via an interactive user interface (e.g., via display 316).

As should be understood, various embodiments provide an improvement over current automated medical information/data analysis. For example, current methods of automated medical information/data analysis include binary encoding an instance of medical information/data that results in each instance of medical information/data having a dimensionality equal to the dimensionality of the set of medical codes. For example, the CPT codes alone define 10,000 codes, and ICD-10 diagnoses define over 70,000 codes. Thus, these binary encodings are of very high dimensionality and fail to capture the similarity between two instances of medical information/data. For example, the diagnosis code for a left arm fracture is different from the diagnosis code for an identical right arm fracture. The binary encodings for a patient with a left arm fracture and another patient with an identical right arm fracture would fail to show the similarity between the two patients' clinical events. Thus, the current automated medical information/data analysis fails to be able to provide models that are efficient in terms of computing and memory resources and that can harness the insight of medical domain knowledge (e.g., that a left arm fracture and an identical right arm fracture are similar medical events). The separation of codes into procedure and diagnosis sets also means that one cannot easily determine that the broken arm is associated with certain radiology, surgery and immobilization procedures. The association among these codes is only possible through advanced methods like these code embeddings.

Moreover, example embodiments provide a model that takes into account a patient's medical history and that can be used to determine an expected outcome of a treatment, prescription, and/or the like for a patient based on the experiences of other, similar patients (e.g., the cohort of second patients and/or the population of patients). Furthermore, likely future medical events for a patient may be predicted based on the experiences of other, similar patients (e.g., the cohort of second patients and/or the population of patients). Additional activities, steps, treatment, and/or the like that the patient may take to improve the patient's health state may also be identified and provided. Thus, various embodiments provide a technical improvement in the field of determining a best course of action for a patient based on the patient's medical history and the experiences of other, similar patients (e.g., the cohort of second patients and/or the population of patients).

As should be understood, automated generation of vector embeddings corresponding to medical codes is more complicated than automated generation of vector embeddings corresponding to words or textual information. In particular, the techniques used for natural language processing tend to fail for processing medical codes as medical codes do not follow a particular grammar. Thus, embodiments of the present invention provide an improvement to computer technology and the technical field of automated processing of medical information/data represented as medical codes. For example, the chronological order of the medical codes in the medical sentences and/or the use of a combining function that takes into account the chronology of medical codes when combining multi-dimensional vectors help to provide a more robust and insightful vector embedding. Thus, embodiments of the present invention provide an improvement to computer technology by providing a technique for expanding the use of embeddings from textual information to general information that does not follow a grammar.

V. Conclusion

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A method for providing a health state of a first patient, the method comprising:
    accessing, by a computing entity comprising a processor and a memory storing computer program code, a plurality of instances of medical information encoded using medical codes and corresponding to a population of patients comprising a plurality of patients;
    generating, by the computing entity, a plurality of medical sentences corresponding to the population of patients by, for each patient of the population of patients, generating one medical sentence based on one or more instances of the plurality of instances of medical information corresponding to the patient and a timestamp associated with each instance of the one or more instances such that the one medical sentence corresponding to the patient comprises one or more medical codes in a chronological order;
    generating, by the computing entity, a vector dictionary comprising a plurality of multi-dimensional vectors (a) based on a vector generation model trained using machine learning and the plurality of medical sentences, and (b) in a multi-dimensional space having a configurable dimensionality, each multi-dimensional vector corresponding to a medical code;
    generating, by the computing entity, a digital representation of a first patient of the population of patients using an anagram model and the multi-dimensional vectors of the vector dictionary;
    determining, by the computing entity, a health state of the first patient based on the digital representation of the first patient; and
    providing, by the computing entity, an output indicating the health state of the first patient.

2. The method of claim 1, wherein each of the plurality of medical sentences comprises a particular number of medical codes.

3. The method of claim 2, further comprising:
    identifying a longest medical sentence of the plurality of medical sentences;
    determining the number of medical codes in the longest medical sentence;
    setting the particular number to the number of medical codes in the longest medical sentence; and
    for any medical sentence of the plurality of medical sentences having a length that is shorter than the particular number, adding dummy codes to the medical sentence until the medical sentence comprises the particular number of medical codes.

4. The method of claim 1, further comprising:
    using an anagram model to simulate a possible future health state of the first patient; and
    providing an output indicating the possible further health state of the first patient.

5. The method of claim 4, wherein the possible future health state of the first patient is at least one of (a) an optimal health state of the first patient given the first patient's medical history, (b) an expected future health state determined based on digital representations of a cohort of patients having similar medical histories as the first patient, or (c) a predicted result of a medical decision for the first patient.

6. The method of claim 4, wherein using an anagram model comprises at least one of (a) combining the digital representation of the first patient with one or more multi-dimensional vectors from the vector dictionary to simulate the possible future health state of the first patient or (b) applying one or more anagram relationships identified within the vector dictionary to the digital representation of the first patient.

7. The method of claim 1, wherein the digital representation of the first patient has a same magnitude as a digital representation of a second patient.

8. The method of claim 1, wherein the vector dictionary is generated by a vector generation model trained using machine learning, wherein at least a portion of the plurality of medical sentences are used as a training set for the machine learning.

9. The method of claim 8, wherein the machine learning uses a predetermined code window.

10. The method of claim 9, wherein the predetermined code window is in the range of 2-10 codes.

11. An apparatus comprising at least one processor and at least one memory including computer program code for one or more programs, the at least one memory and the computer program code configured to, with the at least one processor, cause the apparatus to perform at least the following:
    access a plurality of instances of medical information encoded using medical codes and corresponding to a population of patients comprising a plurality of patients;
    generate a plurality of medical sentences corresponding to the population of patients by, for each patient of the population of patients, generating one medical sentence based on one or more instances of the plurality of instances of medical information corresponding to the patient and a timestamp associated with each instance of the one or more instances such that the one medical sentence corresponding to the patient comprises one or more medical codes in a chronological order;
    generate a vector dictionary comprising a plurality of multi-dimensional vectors (a) based on a vector generation model trained using machine learning and the plurality of medical sentences, and (b) in a multi-dimensional space having a configurable dimensionality, each multi-dimensional vector corresponding to a medical code;
    generate a digital representation of a first patient of the population of patients using an anagram model and the multi-dimensional vectors of the vector dictionary;
    determine a health state of the first patient based on the digital representation of the first patient; and
    provide an output indicating the health state of the first patient.

12. The apparatus of claim 11, wherein each of the plurality of medical sentences comprises a particular number of medical codes.

13. The apparatus of claim 12, wherein the at least one memory and the computer program code are further configured to, with the at least one processor, cause the apparatus to perform at least the following:

identify a longest medical sentence of the plurality of medical sentences;

determine the number of medical codes in the longest medical sentence;

set the particular number to the number of medical codes in the longest medical sentence; and for any medical sentence of the plurality of medical sentences having a length that is shorter than the particular number, add dummy codes to the medical sentence until the medical sentence comprises the particular number of medical codes.

14. The apparatus of claim 11, wherein the at least one memory and the computer program code are further configured to, with the at least one processor, cause the apparatus to perform at least the following:

use an anagram model to simulate a possible future health state of the first patient; and provide an output indicating the possible further health state of the first patient.

15. The apparatus of claim 14, wherein the possible future health state of the first patient is at least one of (a) an optimal health state of the first patient given the first patient's medical history, (b) an expected future health state determined based on digital representations of a cohort of patients having similar medical histories as the first patient, or (c) a predicted result of a medical decision for the first patient.

16. The apparatus of claim 14, wherein using an anagram model comprises at least one of (a) combining the digital representation of the first patient with one or more multi-dimensional vectors from the vector dictionary to simulate the possible future health state of the first patient or (b) applying one or more anagram relationships identified within the vector dictionary to the digital representation of the first patient.

17. The apparatus of claim 11, wherein the digital representation of the first patient has a same magnitude as a digital representation of a second patient.

18. The apparatus of claim 11, wherein the vector dictionary is generated by a vector generation model trained using machine learning, wherein at least a portion of the plurality of medical sentences are used as a training set for the machine learning.

19. The apparatus of claim 18, wherein the machine learning uses a predetermined code window in the range of 2-10 codes.

20. A computer program product comprising at least one non-transitory computer-readable storage medium having computer-executable program code portions stored therein, the computer-executable program code portions comprising program code instructions, the computer program code instructions, when executed by a processor of a computing entity, are configured to cause the computing entity to at least:

access a plurality of instances of medical information encoded using medical codes and corresponding to a population of patients comprising a plurality of patients;

generate a plurality of medical sentences corresponding to the population of patients by, for each patient of the population of patients, generating one medical sentence based on one or more instances of the plurality of instances of medical information corresponding to the patient and a timestamp associated with each instance of the one or more instances such that the one medical sentence corresponding to the patient comprises one or more medical codes in a chronological order;

generate a vector dictionary comprising a plurality of multi-dimensional vectors (a) based on a vector generation model trained using machine learning and the plurality of medical sentences, and (b) in a multi-dimensional space having a configurable dimensionality, each multi-dimensional vector corresponding to a medical code;

generate a digital representation of a first patient of the population of patients using an anagram model and the multi-dimensional vectors of the vector dictionary;

determine a health state of the first patient based on the digital representation of the first patient; and provide an output indicating the health state of the first patient.

\* \* \* \* \*